(12) United States Patent
Esfandiari

(10) Patent No.: US 8,603,835 B2
(45) Date of Patent: Dec. 10, 2013

(54) REDUCED STEP DUAL PATH IMMUNOASSAY DEVICE AND METHOD

(75) Inventor: Javanbakhsh Esfandiari, Stony Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 346 days.

(21) Appl. No.: 13/024,422

(22) Filed: Feb. 10, 2011

(65) Prior Publication Data

US 2012/0208299 A1    Aug. 16, 2012

(51) Int. Cl.
   *G01N 33/558*    (2006.01)

(52) U.S. Cl.
   USPC ........... 436/514; 422/400; 422/401; 422/408; 422/413; 422/414; 422/420; 422/425; 435/287.2; 435/287.6; 435/287.7; 435/287.9; 435/805; 435/810; 435/970; 436/169; 436/518; 436/810

(58) Field of Classification Search
   None
   See application file for complete search history.

(56) References Cited

U.S. PATENT DOCUMENTS

| | | |
|---|---|---|
| 3,960,488 A | 6/1976 | Giaever |
| 4,041,146 A | 8/1977 | Giaever |
| 4,042,335 A | 8/1977 | Clement |
| 4,059,405 A | 11/1977 | Sodickson et al. |
| 4,094,647 A | 6/1978 | Deutsch et al. |
| 4,144,306 A | 3/1979 | Figueras |
| 4,235,601 A | 11/1980 | Deutsch et al. |
| 4,313,734 A | 2/1982 | Leuvering |
| 4,323,536 A | 4/1982 | Columbus |
| 4,361,537 A | 11/1982 | Deutsch et al. |
| 4,366,241 A | 12/1982 | Tom et al. |
| 4,373,932 A | 2/1983 | Gribnau |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |
| 4,668,619 A | 5/1987 | Greenquist et al. |
| 4,703,017 A | 10/1987 | Campbell et al. |
| 4,740,468 A | 4/1988 | Weng et al. |
| 4,770,853 A | 9/1988 | Bernstein |
| 4,786,595 A | 11/1988 | Arai et al. |
| 4,826,759 A | 5/1989 | Guire et al. |
| 4,855,240 A | 8/1989 | Rosenstein et al. |

(Continued)

FOREIGN PATENT DOCUMENTS

| DE | 19917093 | 10/2000 |
|---|---|---|
| DE | 10313158 | 10/2004 |

(Continued)

*Primary Examiner* — Chris L Chin
(74) *Attorney, Agent, or Firm* — Gordon & Jacobson, PC

(57) ABSTRACT

Test cells have a first sorbent strip with a sample receiving location and defining a first migration path, a distinct second sorbent strip which receives buffer solution and at least partially defines a second migration path distinct from and elongated relative to the first migration path, conjugate supported by the second strip, a test site located at a junction of the first and second strips and having an immobilized ligand-binding mechanism, and a divider which directs a first amount of the buffer to the first strip to move the sample to the test site and a second amount to the second strip to move the conjugate to the test site. The first and second migration paths have first and second lengths chosen so that ligand in the sample reaches the test site and binds to the immobilized ligand-binding mechanism prior to the conjugate reaching the test site.

19 Claims, 4 Drawing Sheets

(56) References Cited

U.S. PATENT DOCUMENTS

| | | | |
|---|---|---|---|
| 4,857,453 A | 8/1989 | Ullman et al. | |
| 4,870,003 A | 9/1989 | Kortright et al. | |
| 4,886,742 A | 12/1989 | Kortright et al. | |
| 4,906,439 A | 3/1990 | Grenner | |
| 4,912,034 A | 3/1990 | Kalra et al. | |
| 4,920,046 A | 4/1990 | McFarland et al. | |
| 4,943,522 A * | 7/1990 | Eisinger et al. | 435/7.25 |
| 4,956,275 A | 9/1990 | Zuk et al. | |
| 4,956,302 A | 9/1990 | Gordon et al. | |
| 4,960,691 A * | 10/1990 | Gordon et al. | 435/6.12 |
| 4,960,710 A | 10/1990 | Lau | |
| 4,981,785 A | 1/1991 | Nayak | |
| 4,981,786 A | 1/1991 | Dafforn et al. | |
| 5,004,584 A | 4/1991 | Rayman | |
| 5,006,464 A | 4/1991 | Chu et al. | |
| 5,006,474 A | 4/1991 | Horstman et al. | |
| 5,075,077 A | 12/1991 | Durley, III et al. | |
| 5,087,556 A | 2/1992 | Ertinghausen | |
| 5,091,153 A | 2/1992 | Bachand | |
| 5,104,793 A | 4/1992 | Buck | |
| 5,104,811 A | 4/1992 | Berger et al. | |
| 5,110,550 A | 5/1992 | Schlipfenbacher | |
| 5,132,208 A | 7/1992 | Freitag et al. | |
| 5,137,808 A | 8/1992 | Ullman et al. | |
| 5,147,780 A | 9/1992 | Pouletty et al. | |
| 5,156,952 A | 10/1992 | Litman et al. | |
| 5,162,238 A | 11/1992 | Eikmeier et al. | |
| 5,169,789 A | 12/1992 | Bernstein | |
| 5,173,433 A | 12/1992 | Bachand | |
| 5,200,321 A | 4/1993 | Kidwell | |
| 5,202,268 A | 4/1993 | Kuhn et al. | |
| 5,215,446 A | 6/1993 | Takahashi | |
| 5,217,905 A | 6/1993 | Marchand et al. | |
| 5,219,762 A | 6/1993 | Katamine et al. | |
| 5,223,436 A | 6/1993 | Freitag et al. | |
| RE34,312 E | 7/1993 | Geiger et al. | |
| 5,232,835 A | 8/1993 | Litman et al. | |
| 5,238,649 A | 8/1993 | Nason | |
| 5,240,735 A | 8/1993 | Lau | |
| 5,244,631 A | 9/1993 | Morikawa | |
| 5,244,788 A | 9/1993 | Hubscher | |
| RE34,405 E | 10/1993 | Gould et al. | |
| 5,252,496 A * | 10/1993 | Kang et al. | 436/529 |
| 5,275,785 A | 1/1994 | May et al. | |
| 5,281,540 A | 1/1994 | Merkh et al. | |
| 5,296,192 A | 3/1994 | Carroll et al. | |
| 5,300,439 A | 4/1994 | Charlton | |
| 5,306,623 A | 4/1994 | Kiser et al. | |
| 5,308,775 A | 5/1994 | Donovan et al. | |
| 5,332,548 A | 7/1994 | Moore | |
| 5,334,502 A | 8/1994 | Sangha | |
| 5,338,513 A | 8/1994 | Schlipfenbacher | |
| 5,340,748 A | 8/1994 | Baugher et al. | |
| 5,356,782 A | 10/1994 | Moorman et al. | |
| 5,362,654 A | 11/1994 | Pouletty | |
| 5,369,007 A | 11/1994 | Kidwell | |
| 5,384,264 A | 1/1995 | Chen et al. | |
| 5,391,478 A | 2/1995 | Greene et al. | |
| 5,399,316 A | 3/1995 | Yamada | |
| 5,411,858 A | 5/1995 | McGeeham et al. | |
| 5,418,136 A | 5/1995 | Miller et al. | |
| 5,418,142 A | 5/1995 | Kiser et al. | |
| 5,418,167 A | 5/1995 | Matner et al. | |
| 5,424,215 A | 6/1995 | Albarella et al. | |
| 5,424,220 A | 6/1995 | Goerlach-Graw et al. | |
| 5,435,970 A | 7/1995 | Mamenta et al. | |
| 5,451,504 A | 9/1995 | Fitzpatrick et al. | |
| 5,468,648 A | 11/1995 | Chandler | |
| 5,470,713 A | 11/1995 | El Shami et al. | |
| 5,474,902 A | 12/1995 | Uylen et al. | |
| 5,482,830 A | 1/1996 | Bogart et al. | |
| 5,494,830 A | 2/1996 | Hubscher | |
| 5,500,350 A | 3/1996 | Baker et al. | |
| 5,501,985 A | 3/1996 | Baugher et al. | |
| 5,514,557 A | 5/1996 | Moghaddam | |
| 5,521,102 A | 5/1996 | Boehringer et al. | |
| 5,532,133 A | 7/1996 | Barnwell | |
| 5,541,057 A | 7/1996 | Bogart et al. | |
| 5,550,063 A | 8/1996 | Bogart | |
| 5,552,272 A | 9/1996 | Bogart | |
| 5,558,834 A | 9/1996 | Chu et al. | |
| 5,559,041 A | 9/1996 | Kang et al. | |
| 5,567,594 A | 10/1996 | Calenoff | |
| 5,571,667 A | 11/1996 | Chu et al. | |
| 5,591,645 A | 1/1997 | Rosenstein | |
| 5,602,040 A | 2/1997 | May et al. | |
| 5,604,110 A | 2/1997 | Baker et al. | |
| 5,607,863 A | 3/1997 | Chandler | |
| 5,616,467 A | 4/1997 | Olsen et al. | |
| 5,620,845 A | 4/1997 | Gould et al. | |
| 5,622,871 A | 4/1997 | May et al. | |
| 5,624,809 A | 4/1997 | Skold et al. | |
| 5,629,164 A | 5/1997 | Rivers | |
| 5,629,214 A | 5/1997 | Crosby | |
| 5,639,671 A | 6/1997 | Bogart et al. | |
| 5,641,639 A | 6/1997 | Perry | |
| 5,648,274 A | 7/1997 | Chandler | |
| 5,656,503 A | 8/1997 | May et al. | |
| 5,658,723 A | 8/1997 | Oberhardt | |
| 5,658,801 A | 8/1997 | Poissant et al. | |
| 5,670,381 A | 9/1997 | Jou et al. | |
| 5,686,315 A | 11/1997 | Pronovost | |
| 5,695,928 A | 12/1997 | Stewart et al. | |
| 5,695,930 A | 12/1997 | Weinstein et al. | |
| 5,710,005 A | 1/1998 | Rittenburg | |
| 5,714,341 A | 2/1998 | Thieme et al. | |
| 5,714,389 A | 2/1998 | Charlton et al. | |
| 5,723,345 A | 3/1998 | Yamauchi et al. | |
| 5,726,010 A | 3/1998 | Clark | |
| 5,728,587 A | 3/1998 | Kang et al. | |
| 5,736,188 A | 4/1998 | Alcock et al. | |
| 5,739,041 A | 4/1998 | Nazareth et al. | |
| 5,743,960 A | 4/1998 | Tisone | |
| 5,750,333 A | 5/1998 | Clark | |
| 5,766,961 A | 6/1998 | Pawlak et al. | |
| 5,766,962 A | 6/1998 | Childs et al. | |
| 5,770,460 A | 6/1998 | Pawlak et al. | |
| 5,773,234 A | 6/1998 | Pronovost et al. | |
| 5,786,220 A | 7/1998 | Pronovost et al. | |
| 5,807,756 A | 9/1998 | Bauman et al. | |
| 5,814,522 A | 9/1998 | Zimmer et al. | |
| 5,824,268 A | 10/1998 | Bernstein et al. | |
| 5,827,646 A | 10/1998 | Middeldorp et al. | |
| 5,846,838 A | 12/1998 | Chandler | |
| 5,853,670 A | 12/1998 | Bunce | |
| 5,861,265 A | 1/1999 | Perry | |
| 5,869,272 A | 2/1999 | Bogart et al. | |
| 5,869,345 A | 2/1999 | Chandler | |
| 5,872,713 A | 2/1999 | Douglas et al. | |
| 5,874,216 A | 2/1999 | Mapes | |
| 5,877,028 A | 3/1999 | Chandler et al. | |
| 5,879,951 A | 3/1999 | Sy | |
| 5,885,526 A | 3/1999 | Chu | |
| 5,885,527 A | 3/1999 | Buechler | |
| 5,891,650 A | 4/1999 | Godowski et al. | |
| 5,900,379 A | 5/1999 | Noda et al. | |
| 5,902,722 A | 5/1999 | Di Cesare et al. | |
| 5,912,116 A | 6/1999 | Caldwell | |
| 5,922,533 A | 7/1999 | Vallari et al. | |
| 5,922,615 A | 7/1999 | Nowakowski et al. | |
| 5,935,331 A | 8/1999 | Naka et al. | |
| 5,939,252 A | 8/1999 | Lennon et al. | |
| 5,939,272 A | 8/1999 | Buechler et al. | |
| 5,948,695 A | 9/1999 | Douglas et al. | |
| 5,955,377 A | 9/1999 | Maul et al. | |
| 5,958,790 A | 9/1999 | Cerny | |
| 5,965,458 A | 10/1999 | Kouvonen et al. | |
| 5,972,720 A | 10/1999 | Nichtl et al. | |
| 5,976,895 A | 11/1999 | Cipkowski | |
| 5,985,675 A | 11/1999 | Charm et al. | |
| 5,989,921 A | 11/1999 | Charlton et al. | |
| 5,998,220 A | 12/1999 | Chandler | |
| 5,998,221 A | 12/1999 | Malick et al. | |
| 6,008,056 A | 12/1999 | Thieme | |

(56) References Cited

U.S. PATENT DOCUMENTS

| | | |
|---|---|---|
| 6,017,767 A | 1/2000 | Chandler |
| 6,027,890 A | 2/2000 | Ness et al. |
| 6,040,195 A | 3/2000 | Carroll et al. |
| 6,046,013 A | 4/2000 | Tidey et al. |
| 6,046,057 A | 4/2000 | Nazareth et al. |
| 6,057,166 A | 5/2000 | Childs et al. |
| 6,060,326 A | 5/2000 | Frank et al. |
| 6,063,337 A | 5/2000 | Markart |
| 6,087,184 A | 7/2000 | Magginetti et al. |
| 6,106,732 A | 8/2000 | Johnston et al. |
| 6,140,134 A | 10/2000 | Rittenburg |
| 6,140,136 A | 10/2000 | Lee |
| 6,168,956 B1 | 1/2001 | Chandler |
| 6,187,268 B1 | 2/2001 | Albarella et al. |
| 6,187,598 B1 | 2/2001 | May et al. |
| 6,194,220 B1 | 2/2001 | Malick et al. |
| 6,197,494 B1 | 3/2001 | Oberhardt |
| 6,221,625 B1 | 4/2001 | Ashihara et al. |
| 6,221,678 B1 | 4/2001 | Chandler |
| 6,224,831 B1 | 5/2001 | Stafford et al. |
| 6,228,660 B1 | 5/2001 | May et al. |
| 6,235,464 B1 | 5/2001 | Henderson et al. |
| 6,248,598 B1 | 6/2001 | Bogema |
| 6,258,548 B1 | 7/2001 | Buck |
| 6,271,040 B1 | 8/2001 | Buechler |
| 6,271,045 B1 | 8/2001 | Douglas et al. |
| 6,271,046 B1 | 8/2001 | Chandler |
| 6,277,650 B1 | 8/2001 | Nazareth et al. |
| 6,284,550 B1 | 9/2001 | Carroll et al. |
| 6,287,875 B1 | 9/2001 | Geisberg |
| 6,297,020 B1 | 10/2001 | Brock |
| 6,297,060 B1 | 10/2001 | Nowakowski et al. |
| 6,300,142 B1 | 10/2001 | Andrewes et al. |
| RE37,437 E | 11/2001 | Friesen et al. |
| 6,316,205 B1 | 11/2001 | Guan et al. |
| 6,316,264 B1 | 11/2001 | Corey et al. |
| 6,319,676 B1 | 11/2001 | Nazareth et al. |
| 6,326,214 B1 | 12/2001 | Liu et al. |
| 6,335,205 B1 | 1/2002 | Bausback |
| 6,352,862 B1 | 3/2002 | Davis et al. |
| 6,362,008 B1 | 3/2002 | Kohn et al. |
| 6,368,875 B1 | 4/2002 | Geisberg |
| 6,368,876 B1 | 4/2002 | Huang et al. |
| 6,372,514 B1 | 4/2002 | Lee |
| 6,372,515 B1 | 4/2002 | Casterlin et al. |
| 6,372,516 B1 | 4/2002 | Sun |
| 6,376,195 B1 | 4/2002 | Mapes |
| 6,399,398 B1 | 6/2002 | Cunningham et al. |
| 6,403,383 B1 | 6/2002 | Casterlin et al. |
| 6,403,384 B1 | 6/2002 | Lea |
| 6,406,922 B2 | 6/2002 | Casterlin et al. |
| 6,413,473 B1 | 7/2002 | Bacon |
| 6,413,784 B1 | 7/2002 | Lundsgaard et al. |
| 6,436,722 B1 | 8/2002 | Clark et al. |
| 6,455,324 B1 | 9/2002 | Douglas |
| 6,472,226 B1 | 10/2002 | Barradine et al. |
| 6,475,805 B1 | 11/2002 | Charm et al. |
| 6,485,982 B1 | 11/2002 | Charlton |
| 6,489,129 B1 | 12/2002 | Faatz et al. |
| 6,492,127 B2 | 12/2002 | Goodell et al. |
| 6,500,629 B1 | 12/2002 | Cleaver et al. |
| 6,502,766 B1 | 1/2003 | Streutker et al. |
| 6,503,702 B1 | 1/2003 | Stewart |
| 6,503,722 B1 | 1/2003 | Valkirs |
| 6,511,814 B1 | 1/2003 | Carpenter |
| 6,514,769 B2 | 2/2003 | Lee |
| 6,514,773 B1 | 2/2003 | Klein et al. |
| 6,528,321 B1 | 3/2003 | Fitzgerald et al. |
| 6,528,322 B1 | 3/2003 | Carlsson et al. |
| 6,528,323 B1 | 3/2003 | Thayer et al. |
| 6,528,325 B1 | 3/2003 | Hubscher et al. |
| 6,534,324 B1 | 3/2003 | Zin |
| 6,544,474 B2 | 4/2003 | Douglas |
| 6,548,309 B1 | 4/2003 | Moore et al. |
| 6,551,842 B1 | 4/2003 | Carpenter |
| 6,592,815 B1 | 7/2003 | Zimmer |
| 6,593,085 B1 | 7/2003 | Barnett et al. |
| 6,602,719 B1 | 8/2003 | Carpenter |
| 6,617,116 B2 | 9/2003 | Guan et al. |
| 6,623,955 B2 | 9/2003 | Matner et al. |
| 6,627,459 B1 | 9/2003 | Tung et al. |
| 6,632,681 B1 | 10/2003 | Chu |
| 6,645,732 B2 | 11/2003 | Faatz et al. |
| 6,649,418 B1 | 11/2003 | Geisberg |
| 6,656,744 B2 | 12/2003 | Pronovost et al. |
| 6,656,745 B1 | 12/2003 | Cole |
| 6,660,469 B1 | 12/2003 | Wright et al. |
| 6,663,833 B1 | 12/2003 | Stave et al. |
| 6,673,628 B2 | 1/2004 | Freitag et al. |
| RE38,430 E | 2/2004 | Rosenstein |
| 6,686,167 B2 | 2/2004 | Bagaria |
| 6,699,722 B2 | 3/2004 | Bauer et al. |
| 6,703,196 B1 | 3/2004 | Klepp et al. |
| 6,706,539 B2 | 3/2004 | Nelson et al. |
| 6,713,309 B1 | 3/2004 | Anderson et al. |
| 6,727,073 B1 | 4/2004 | Moore et al. |
| 6,737,277 B1 | 5/2004 | Kang et al. |
| 6,750,031 B1 | 6/2004 | Ligler et al. |
| 6,753,190 B1 | 6/2004 | Okada et al. |
| 6,767,710 B2 | 7/2004 | DiNello et al. |
| 6,767,714 B2 | 7/2004 | Nazareth et al. |
| 6,780,651 B2 | 8/2004 | Douglas et al. |
| 6,790,611 B2 | 9/2004 | Lassen et al. |
| 6,797,481 B1 | 9/2004 | Ullman et al. |
| 6,808,889 B2 | 10/2004 | Fitzpatrick et al. |
| 6,808,937 B2 | 10/2004 | Ligler et al. |
| 6,812,038 B1 | 11/2004 | Mendel-Hartvig et al. |
| 6,818,180 B2 | 11/2004 | Douglas et al. |
| 6,818,455 B2 | 11/2004 | May et al. |
| 6,824,975 B2 | 11/2004 | Hubscher et al. |
| 6,824,997 B1 | 11/2004 | Moore et al. |
| 6,828,110 B2 | 12/2004 | Lee et al. |
| RE38,688 E | 1/2005 | Friesen et al. |
| 6,844,200 B2 | 1/2005 | Brock |
| 6,846,635 B1 | 1/2005 | Anderson et al. |
| 6,849,414 B2 | 2/2005 | Guan et al. |
| 6,855,561 B2 | 2/2005 | Jerome et al. |
| 6,863,866 B2 | 3/2005 | Kelly et al. |
| 6,867,051 B1 | 3/2005 | Anderson et al. |
| 6,887,701 B2 | 5/2005 | Anderson et al. |
| 6,905,835 B2 | 6/2005 | Sorell Gomez et al. |
| 6,924,153 B1 | 8/2005 | Boehringer et al. |
| 6,927,068 B2 | 8/2005 | Simonson et al. |
| 6,991,940 B2 | 1/2006 | Carroll et al. |
| 7,018,847 B2 | 3/2006 | Mendel-Hartvig et al. |
| 7,045,342 B2 | 5/2006 | Nazareth et al. |
| 7,049,130 B2 | 5/2006 | Carroll et al. |
| 7,109,042 B2 | 9/2006 | May et al. |
| 7,189,522 B2 | 3/2007 | Esfandiari |
| 7,270,995 B2 | 9/2007 | Matsushita et al. |
| 7,682,801 B2 | 3/2010 | Esfabdiari |
| 7,879,597 B2 | 2/2011 | Esfandiari |
| 2001/0012637 A1 | 8/2001 | Casterlin et al. |
| 2001/0026942 A1 | 10/2001 | Carpenter et al. |
| 2001/0026944 A1 | 10/2001 | Chung et al. |
| 2001/0034068 A1 | 10/2001 | Spivey et al. |
| 2001/0039057 A1 | 11/2001 | Douglas et al. |
| 2001/0048893 A1 | 12/2001 | Norris et al. |
| 2002/0001853 A1 | 1/2002 | Obremski et al. |
| 2002/0015663 A1 | 2/2002 | Goldstein et al. |
| 2002/0019062 A1 | 2/2002 | Lea et al. |
| 2002/0031839 A1 | 3/2002 | McNeirney et al. |
| 2002/0046614 A1 | 4/2002 | Alley |
| 2002/0048819 A1 | 4/2002 | Alley |
| 2002/0052050 A1 | 5/2002 | Douglas et al. |
| 2002/0057991 A1 | 5/2002 | Kelly et al. |
| 2002/0058330 A1 | 5/2002 | Carroll et al. |
| 2002/0110803 A1 | 8/2002 | Dhar et al. |
| 2002/0119497 A1 | 8/2002 | Wild et al. |
| 2002/0142291 A1 | 10/2002 | Bauer et al. |
| 2002/0155028 A1 | 10/2002 | Wong |
| 2002/0172937 A1 | 11/2002 | Dave et al. |
| 2002/0173050 A1 | 11/2002 | DiNello et al. |
| 2002/0192839 A1 | 12/2002 | Mink et al. |

(56) References Cited

U.S. PATENT DOCUMENTS

| | | |
|---|---|---|
| 2003/0045001 A1 | 3/2003 | Burgess et al. |
| 2003/0118480 A1 | 6/2003 | Kaylor et al. |
| 2003/0124740 A1 | 7/2003 | Bachand |
| 2003/0138351 A1 | 7/2003 | Etes et al. |
| 2003/0143639 A1 | 7/2003 | Matsushita et al. |
| 2003/0180967 A1 | 9/2003 | Shigetoh |
| 2004/0001767 A1 | 1/2004 | Peters et al. |
| 2004/0087036 A1 | 5/2004 | Chung et al. |
| 2004/0142495 A1 | 7/2004 | Hartman et al. |
| 2004/0161859 A1 | 8/2004 | Guo et al. |
| 2004/0184954 A1 | 9/2004 | Guo et al. |
| 2004/0219694 A1 | 11/2004 | Chittock et al. |
| 2004/0235189 A1 | 11/2004 | Lu |
| 2004/0241779 A1 | 12/2004 | Piasio et al. |
| 2004/0248322 A1 | 12/2004 | Charlton |
| 2005/0074900 A1 | 4/2005 | Morgan et al. |
| 2005/0079629 A1 | 4/2005 | Guo et al. |
| 2005/0112779 A1 | 5/2005 | Wei et al. |
| 2005/0112780 A1 | 5/2005 | Song |
| 2005/0112782 A1 | 5/2005 | Buechler |
| 2005/0130293 A1 | 6/2005 | Blatt et al. |
| 2005/0130319 A1 | 6/2005 | Biegelsen et al. |
| 2005/0136500 A1 | 6/2005 | Yang et al. |
| 2005/0142032 A1 | 6/2005 | Hoenes et al. |
| 2005/0164404 A1 | 7/2005 | Marlborugh et al. |
| 2005/0170527 A1 | 8/2005 | Boehringer et al. |
| 2005/0208677 A1 | 9/2005 | Owens et al. |
| 2005/0227371 A1 | 10/2005 | Gokhan |
| 2005/0244985 A1 | 11/2005 | Freitag et al. |
| 2005/0244986 A1 | 11/2005 | May et al. |
| 2006/0099719 A1 | 5/2006 | Curcio |
| 2006/0121626 A1 | 6/2006 | Imrich |
| 2006/0134803 A1 | 6/2006 | Esfandiari |
| 2006/0166374 A1 | 7/2006 | Hubscher |
| 2007/0020768 A1 | 1/2007 | Rundstrom et al. |
| 2007/0184492 A1 | 8/2007 | Wang et al. |
| 2007/0243630 A1 | 10/2007 | Boehringer et al. |
| 2008/0318341 A1 | 12/2008 | Esfandiari |
| 2009/0148933 A1 | 6/2009 | Battrell et al. |
| 2012/0003727 A1 | 1/2012 | Esfandiari |

FOREIGN PATENT DOCUMENTS

| | | |
|---|---|---|
| EP | 0299359 | 1/1989 |
| EP | 1284422 | 2/2003 |
| JP | 05104052 | 4/1993 |
| WO | WO88/08534 | 11/1988 |
| WO | WO2004/084274 | 9/2004 |
| WO | WO2005/070324 | 8/2005 |

\* cited by examiner

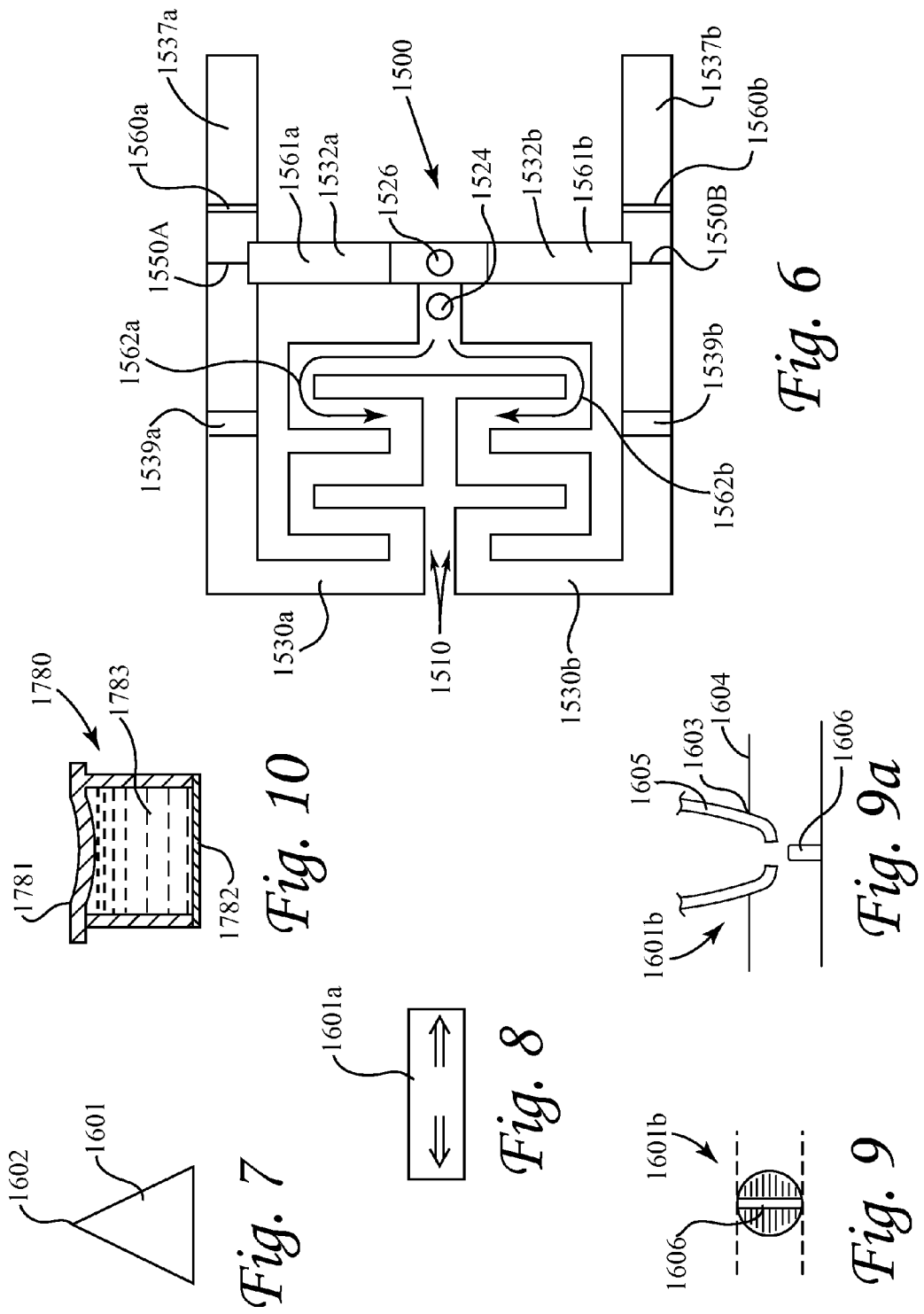

REDUCED STEP DUAL PATH IMMUNOASSAY DEVICE AND METHOD

RELATED APPLICATIONS

This application relates to PCT/US2006/008688 filed Mar. 10, 2006 published as WO 2006/099191 A2, U.S. Ser. No. 11/908,071 filed Sep. 7, 2007, and U.S. Ser. No. 61/338,303 filed Feb. 16, 2010 all of which are hereby incorporated by reference herein in their entireties.

BACKGROUND OF THE INVENTION

1. Field of the Invention

This invention relates broadly to immunoassay devices and the methods for their use. More particularly, this invention relates to chromatographic rapid test strips for detection of a ligand in a body fluid.

2. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Even the qualitative assays must be very sensitive because of the often small concentration of the ligand of interest in the test fluid. False positives can also be troublesome, particularly with agglutination and other rapid detection methods such as dipstick and color change tests. Because of these problems, so-called "sandwich" assays and other sensitive detection mechanisms which use metal sols or other types of colored particles have been developed.

In a "sandwich" assay, a target analyte such as an antigen is "sandwiched" between a labeled antibody and an antibody immobilized onto a solid support. The assay is read by observing the presence and/or amount of bound antigen-labeled antibody complex. In a "competition" immunoassay, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other assays can detect both antibodies and antigens, they are generally referred to as immunochemical ligand-receptor assays or simply immunoassays.

Solid phase immunoassay devices, whether of the sandwich or competition type, provide sensitive detection of an analyte in a biological fluid sample such as blood, urine, or saliva. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. In the last decade, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

In the more common forms of dipstick assays, as typified by home pregnancy and ovulation detection kits, immunochemical components such as antibodies are bound to a solid phase. The assay device is "dipped" for incubation into a sample suspected of containing unknown antigen analyte. Enzyme-labeled antibody is then added, either simultaneously or after an incubation period. The device is then washed and inserted into a second solution containing a substrate for the enzyme. The enzyme-label, if present, interacts with the substrate, causing the formation of colored products which either deposit as a precipitate onto the solid phase or produce a visible color change in the substrate solution.

Flow-through type immunoassay devices were designed to obviate the need for extensive incubation and cumbersome washing steps associated with dipstick assays. Valkirs et al., U.S. Pat. No. 4,632,901, disclose a device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

The requirement of multiple addition and washing steps with dipstick and flow-through type immunoassay devices increases the likelihood that minimally trained personnel and home users will obtain erroneous assay results.

In migration type assays, a membrane is impregnated with the reagents needed to perform the assay. An analyte detection zone is provided in which labeled analyte is bound and assay indicia is read. See, for example, Tom et al., U.S. Pat. No. 4,366,241, and Zuk, et al. U.S. Pat. No. 4,596,275. The sensitivity of migration type assays is frequently reduced, however, by the presence or formation in the sample of undesirable solid components which block the passage of labeled analyte to the detection zone. Assay sensitivity also declines when migration assay devices are flooded with too much liquid sample.

Migration assay devices usually incorporate within them reagents which have been attached to colored labels (i.e., conjugates), thereby permitting visible detection of the assay results without addition of further substances. See, for example, Bernstein, U.S. Pat. No. 4,770,853. Among such labels are gold sol particles such as those described by Leuvering in U.S. Pat. No. 4,313,734, dye sol particles such as described in U.S. Pat. No. 4,373,932 by Gribnau et al., dyed latex such as described by May et al., WO 88/08534, and dyes encapsulated in liposomes by Campbell et al., U.S. Pat. No. 4,703,017. These colored labels are generally limited in terms of the immobilization methods which are suitable. Moreover, they require a relatively large amount of ligand molecule and can involve expensive reagents, thereby adding to the cost.

The "Related Applications" set forth above overcome many deficiencies of the prior art by providing "dual path" immunoassays which are highly sensitive, extremely reliable, accurate and inexpensive rapid detection devices. Generally, the dual path immunoassays include a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and a test line or test site with immobilized antigens or antibodies or other ligand binding molecules such as aptamers, nucleic acids, etc. located in a test zone at a junction of the first and second sorbent materials.

Various types of samples are effectively tested using the duel path immunoassays, including but not limited to whole blood, blood serum, urine, sputum, saliva, and feces. For most samples it is common to utilize buffer solution to cause the sample to flow along the second sorbent material. Thus, one method of using a dual path immunoassays involves (1) depositing a sample at the (second) location for receiving the sample, (2) depositing buffer solution at the same location of the sample, (3) waiting a period of time sufficient to permit the sample to reach the test zone, (4) after waiting, depositing additional buffer solution at the (first) location for receiving the buffer solution such that the additional buffer solution causes the conjugate to flow to the test zone, and (5) inspecting the test zone to determine whether the test is positive or negative.

SUMMARY OF THE INVENTION

According to one aspect of the invention, a rapid detection dual path immunoassay device is provided that requires fewer steps to use than the previous dual path immunoassay devices.

According to another aspect of the invention, a dual path immunoassay device is provided that is simple to use and provides accurate results.

In one embodiment, a dry conjugate dual path immunoassay device system is provided and includes a test cell with a first location for receiving a sample and a second location for receiving a buffer solution. A first sorbent material is provided for directing a horizontal flow path for the sample. Means are provided for dividing the buffer solution received at the second location such that some of the buffer solution is directed to the first sorbent material which directs the sample, and some of the buffer solution is directed to a second sorbent material. In one embodiment, the second sorbent material takes an elongated path (e.g., curved, angled, or tortuous path) to the test zone which is located at the junction of the elongated path of the second sorbent material with the first sorbent material. In another embodiment, the second sorbent material is provided with a delay element along its length. In yet another embodiment, second and third sorbent materials are provided with the third sorbent material initially receiving the buffer solution and having a slower flow characteristic than the first sorbent material, and the second sorbent material in contact with the third sorbent material and forwarding the buffer solution to the test zone which is located at the junction of the second sorbent material and the first sorbent material. Regardless, conjugate is provided at a location along the second sorbent material. Preferably, the flow path provided by the first sorbent material is a direct path to the test zone. The test zone preferably includes one or more test lines or test sites with immobilized antigens or antibodies or other ligand binding molecules such as aptamers, nucleic acids, etc.

Where the test cell of the invention is provided in a housing, the housing is provided with a first opening adjacent the first location and a second opening adjacent the second location. A viewing window is provided in the housing above the test line.

Various means for dividing the buffer solution received at the second location are provided. A first means for dividing the buffer solution is a wedge element (V-shaped or triangular in cross-section) located at the location for receiving the buffer solution (e.g., an opening in a housing), where the apex of the V or triangle is directed upward. As drops of buffer solution are dropped into the buffer receiving opening, the apex divides the drops into two streams. The first stream is directed to the first sorbent material. The second stream is directed to the second elongated path sorbent material.

A second means for dividing the buffer solution received at the second location is a flow control material which is chosen to permit buffer to flow but which is resistant to receiving sample. The flow control material is coupled to both the first and second sorbent materials.

A third means for dividing the buffer solution received at the second location is an arrangement where the second location is an opening in a housing sized to receive the nib of a buffer dispenser, and a vertical wall recessed in the housing opening is provided to divide the buffer solution. Preferably, the first sorbent material is provided on one side of the vertical wall, and the second sorbent material is provided on the other side of the vertical wall.

According to one aspect of the invention, the means for dividing the buffer solution may be arranged so that approximately half of the buffer solution is directed toward the first sorbent material and the other half of the buffer solution is directed toward the second sorbent material.

According to another aspect of the invention, the means for dividing the buffer solution may be arranged so that a desired first proportion of the buffer solution is directed toward the first sorbent material and a desired different second proportion of the buffer solution is directed toward the second sorbent material.

In one embodiment, the locations for receiving the sample and the buffer solution are near or adjacent each other.

In the preferred embodiment of the invention, the first sorbent material and second sorbent material are separate pieces which overlie one another at the test site junction, and the test line is printed on one or both of the sorbent materials at the junction. The systems of the invention preferably also include a control line or site which may be seen from the viewing window.

According to one aspect of the invention, a test cell as summarized above may be used by (1) depositing a sample at the (first) location for receiving the sample, (2) depositing buffer solution at the (second) location for receiving the buffer solution, and (3) after a desired period of time, inspecting the test zone to determine whether the test is positive or negative. It is noted that sufficient buffer is deposited at the second location to cause the sample to move along the first sorbent material to the test zone, as well as to traverse the path of the second (and where provided, third) sorbent material and cause the conjugate to move to the test zone. Because of the arrangement of the first sorbent material as well as the second (and where provided, third) sorbent material, the sample is brought to the test zone in advance of the conjugate.

In one embodiment of the invention, the materials, thicknesses and lengths of the first and second sorbent materials are chosen to adjust the timing regarding the sample and conjugate reaching the test site.

In a fourth generation assay, two paths are provided for directing sample to two test zones, and two elongated paths are provided for carrying buffer and conjugate to the test zones. A first test zone is provided at the intersection of one of the elongated paths with one of the two sample paths, and a second test zone is provided at an intersection of the other elongated path and the second of the sample paths. In the fourth generation assay, one of the test zones may test for antigens in the sample while the other of the test zones may test for antibodies in the sample.

Additional objects and advantages of the invention will become apparent to those skilled in the art upon reference to the detailed description taken in conjunction with the provided figures.

BRIEF DESCRIPTION OF THE DRAWINGS

FIG. 6 is a schematic view of a sixth embodiment of the invention.

FIG. 7 is a side view of a first embodiment of a buffer divider.

FIG. 8 is a top view of a second embodiment of a buffer divider.

FIG. 9 is a top view of a third embodiment of a buffer divider without the dropper.

FIG. 9a is a side view of the third embodiment of the buffer divider.

FIG. 10 is a cross-sectional view of a buffer button.

DETAILED DESCRIPTION OF THE PREFERRED EMBODIMENTS

Before turning to the Figures, the previously incorporated applications are noted as providing examples of dual path immunoassay devices relevant to the present invention. In particular, many of the same elements described in the embodiments of the previously incorporated applications are utilized as the building blocks for the embodiments of the invention which are further described below. As a result, details of those elements are not further described, and attention may be paid to those applications for those details.

Figure 1:
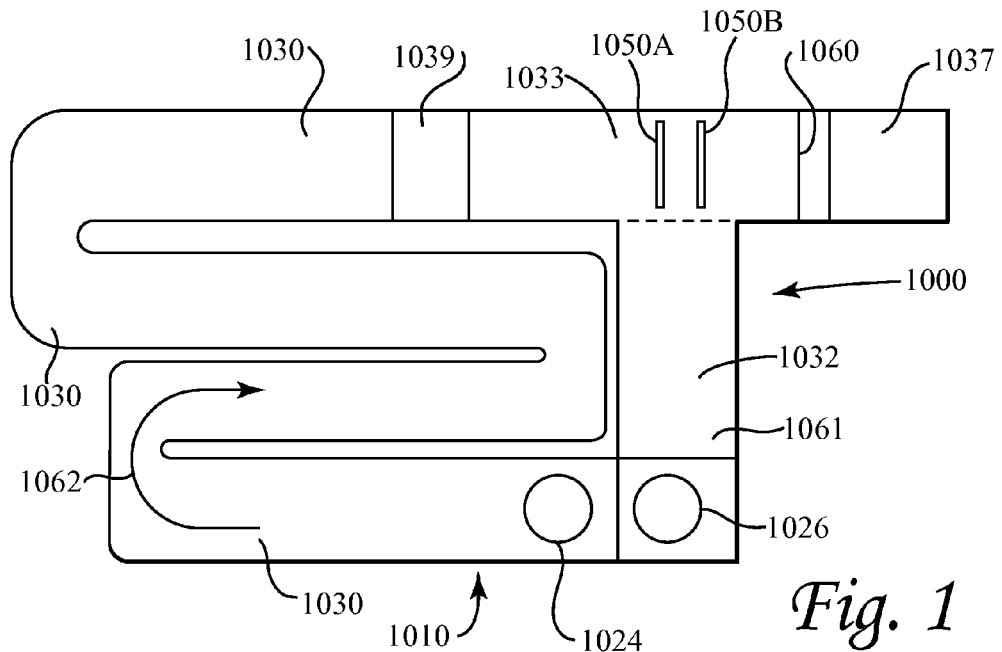
FIG. 1 is a schematic view of a first embodiment of the invention.

Turning now to FIG. 1, a first embodiment of a dry conjugate dual path immunoassay device system 1000 is provided. System 1000 and includes a test cell 1010 with a first location 1026 for receiving a sample and a second location 1024 for receiving a buffer solution. A first sorbent or bibulous material 1032 is provided for directing a horizontal flow path 1061 for the sample. Means discussed below with reference to FIGS. 7-9b are provided for dividing the buffer solution received at the second location 1024 such that some of the buffer solution is directed to the first sorbent material 1032 which directs the sample, and some of the buffer solution is directed to a second sorbent or bibulous material 1030. In the embodiment of FIG. 1, the second sorbent material 1030 is seen to take an elongated path 1062 to the test zone 1033 which is located at the junction of the elongated path of the second sorbent material 1030 with the first sorbent material 1032. The test zone 1033 includes one or more test lines or indicators (e.g., 1050A, 1050B) having immobilized antigens or antibodies on either sorbent material 1030 or sorbent material 1032. Preferably, a control line 1060 is provided downstream of the test line(s), and an optional reservoir or wicking zone 1037 may be provided as well. Conjugate 1039 having desired antigens or antibodies with attached colored markers is immobilized along the elongated path 1062 in or on the second sorbent material 1030 upstream of the test zone 1033. As shown in FIG. 1, the conjugate 1039 is preferably located toward the test zone end of the elongated path. The elongated path 1062 of the second sorbent material 1030 of FIG. 1 is shown to be tortuous and more than five times the length of the horizontal flow path 1061 for the sample. In this manner, if sample is first deposited into the first location 1026, and buffer is then deposited in the second location 1024, the buffer will cause the sample to reach the test zone 1033 via path 1061 and permit antigens or antibodies in the sample to bind to the antibodies or antigens in the test lines 1050A, 1050B in advance of the conjugate 1039 being carried by buffer reaching the test zone via the elongated path 1062.

Figure 2:
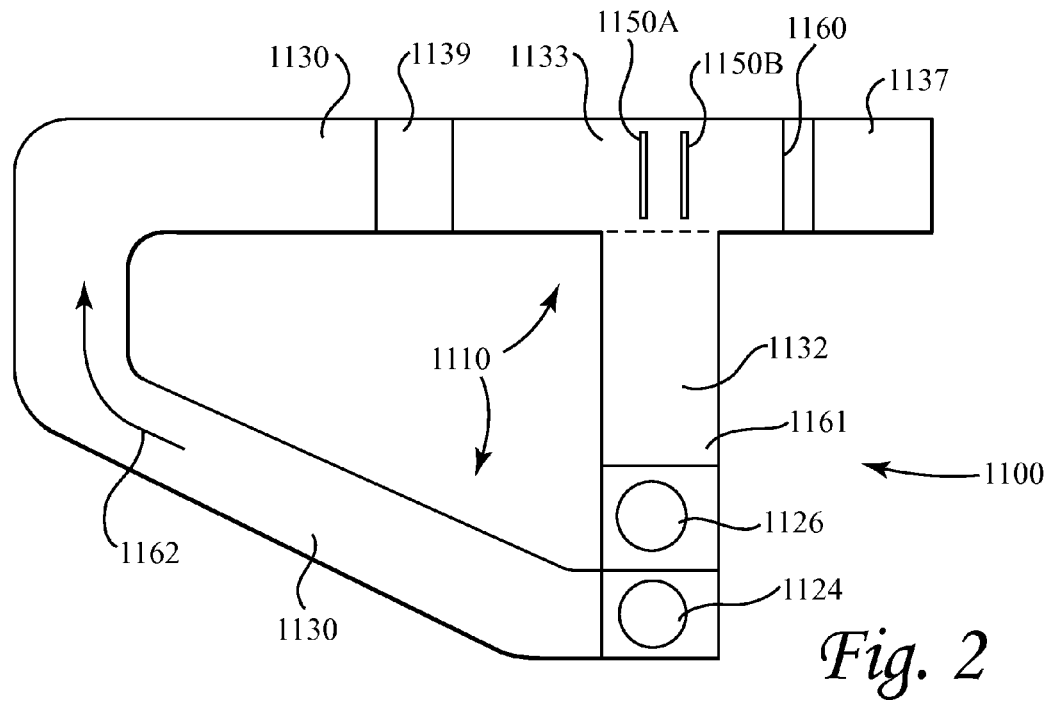
FIG. 2 is a schematic view of a second embodiment of the invention.

A second embodiment of a dry conjugate dual path immunoassay device system 1100 is seen in FIG. 2. System 1100 and includes a test cell 1110 with a first location 1126 for receiving a sample and a second location 1124 for receiving a buffer solution. A first sorbent or bibulous material 1132 is provided for directing a horizontal flow path 1161 for the sample. Means discussed below with reference to FIGS. 7-9b are provided for dividing the buffer solution received at the second location 1124 such that some of the buffer solution is directed to the first sorbent material 1132 which directs the sample, and some of the buffer solution is directed to a second sorbent or bibulous material 1130. In the embodiment of FIG. 2, the second sorbent material 1130 is seen to take an elongated path 1162 to the test zone 1133 which is located at the junction of the elongated path of the second sorbent material 1130 with the first sorbent material 1132. The test zone 1133 includes one or more test lines or indicators (e.g., 1150A, 1150B) having immobilized antigens or antibodies on either sorbent material 1130 or sorbent material 1132. Preferably, a control line 1160 is provided downstream of the test line(s), and an optional reservoir or wicking zone 1137 may be provided as well. Conjugate 1139 having desired antigens or antibodies with attached colored markers is immobilized along the elongated path 1162 in or on the second sorbent material 1130 upstream of the test zone 1133. As shown in FIG. 1, the conjugate 1139 is preferably located toward the test zone end of the elongated path. The elongated path 1162 of the second sorbent material 1130 of FIG. 1 is shown to be curved and approximately four times the length of the horizontal flow path 1161 for the sample. In this manner, if sample is first deposited into the first location 1126, and buffer is then deposited in the second location 1124, the buffer will cause the sample to reach the test zone 1133 via path 1161 and permit antigens or antibodies in the sample to bind to the antibodies or antigens in the test lines 1150A, 1150B in advance of the conjugate 1139 being carried by buffer reaching the test zone via the elongated path 1162.

Figure 3A:
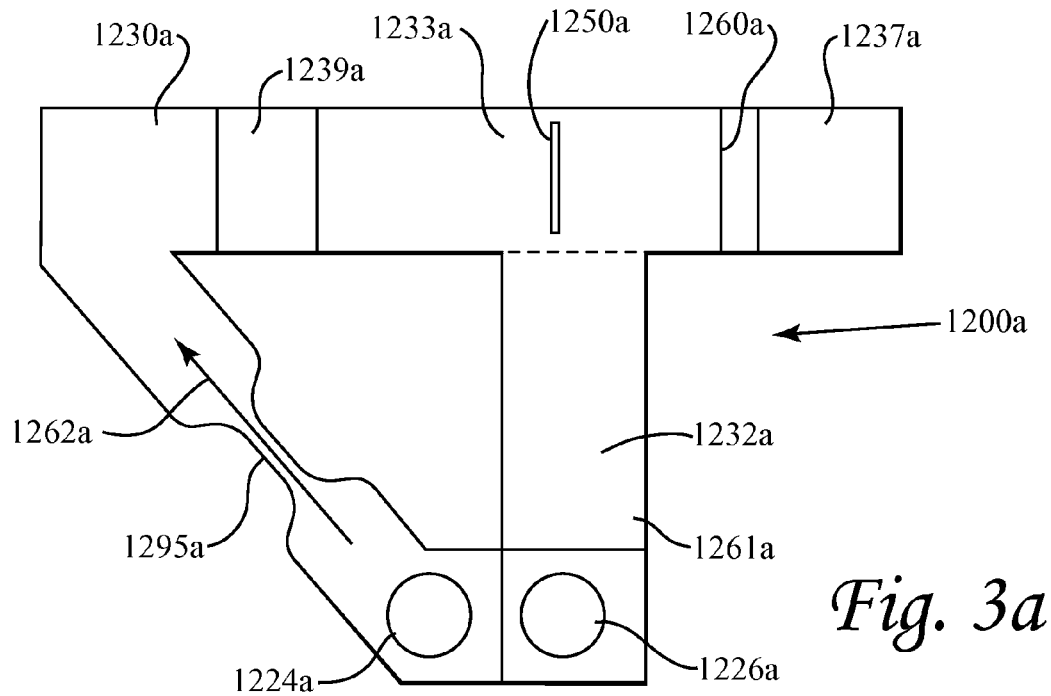
FIG. 3a is a schematic view of a third embodiment of the invention.
Figure 3B:
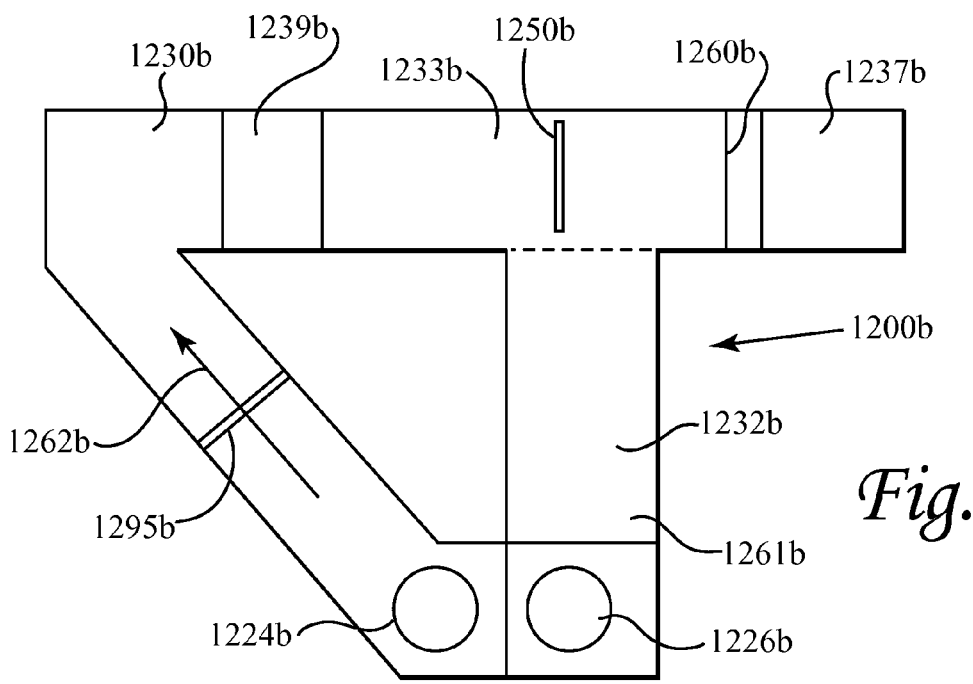
FIG. 3b is a schematic view of an alternative third embodiment of the invention.

Alternate third embodiments of a dry conjugate dual path immunoassay device system 1200a, 1200b are seen in FIGS. 3a and 3b. The alternate third embodiments are similar to the second embodiment system 1100 except that the instead of providing elongated paths 1262a, 1262b for the buffer which are approximately four times the length of the sample paths 1261a, 1261b, the curved paths 1262a, 1262b are about twice as long as the sample paths, but are provided with a delay element 1295a, 1295b along their lengths. In the embodiment of FIG. 3a, the delay element 1295a is a narrowing or bottleneck in the flow path which limits the flow capacity there-through. In the embodiment of FIG. 3b, the delay element 1295b is a viscous material (e.g., sugar) or a blocking agent (e.g., BSA—bovine serum albumin). Delay element 1295b is utilized to delay the flow of buffer along the second sorbent material 1230a, 1230b such that buffer deposited into the second location 1216a, 1216b (and divided by means discussed below with reference to FIGS. 7-9b) will cause the sample deposited into the first location 1226a, 1226b to reach the test zone 1233a, 1233b via path 1261a, 1261b and permit antigens or antibodies in the sample to bind to the antibodies or antigens in the test line 1250a, 1250b in advance of the conjugate 1239a, 1239b being carried by buffer reaching the test zone via the elongated path 1262a, 1262b which includes the delay element 1295a, 1295b. In addition, if desired, multiple delay elements may be provided along the second sorbent material. The alternate third embodiments also preferably include control lines in zones 1250a, 1250b and wicking zones 1237a, 1237b.

Figure 4:
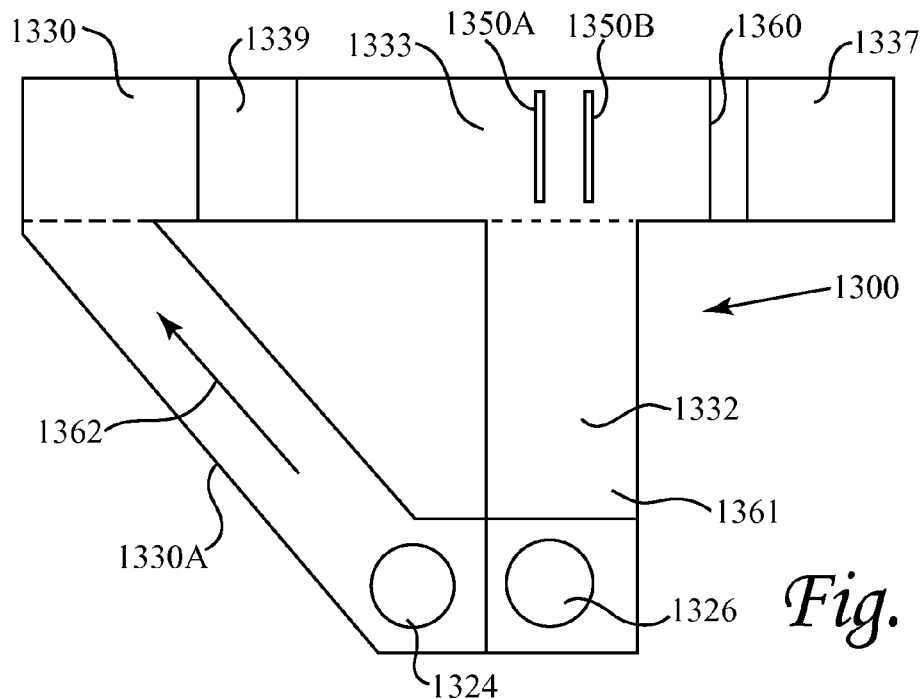
FIG. 4 is a schematic view of a fourth embodiment of the invention.

A fourth embodiment of a dry conjugate dual path immunoassay device system 1300 is seen in FIG. 4. The fourth embodiment is similar to the alternate third embodiment systems 1200a, 1200b except that the instead of providing a delay element along the length second sorbent or bibulous material, a third sorbent or bibulous material 1330A is provided between the second receiving location 1324 and the second sorbent material 1330. The third sorbent material 1330A is selected to have a slower flow characteristic than either the first sorbent material 1332 or the second sorbent material 1330. The conjugate material 1339 is preferably located along the second sorbent material 1330, although it could be located along the third sorbent material 1330A. The test zone 1333 with one or more test lines 1350A, 1350B is located at the intersection of the first sorbent material 1332 and the second sorbent material 1330, and a control zone 1360 with a control indicator as well as a wicking zone 1337 are preferably provided downstream of the test zone 1333. With the provided arrangement, if sample is first deposited into the first location 1326, and buffer is then deposited in the second location 1324 (and divided by means discussed below with reference to FIGS. 7-9b), the buffer will cause the sample to reach the test zone 1333 via path 1361 and permit antigens or antibodies in the sample to bind to the antibodies or antigens in the test lines 1350A, 1350B in advance of the conjugate 1339 being carried by buffer reaching the test zone via the elongated path 1362 which includes the third sorbent material 1330A and the second sorbent material 1330.

Figure 5:
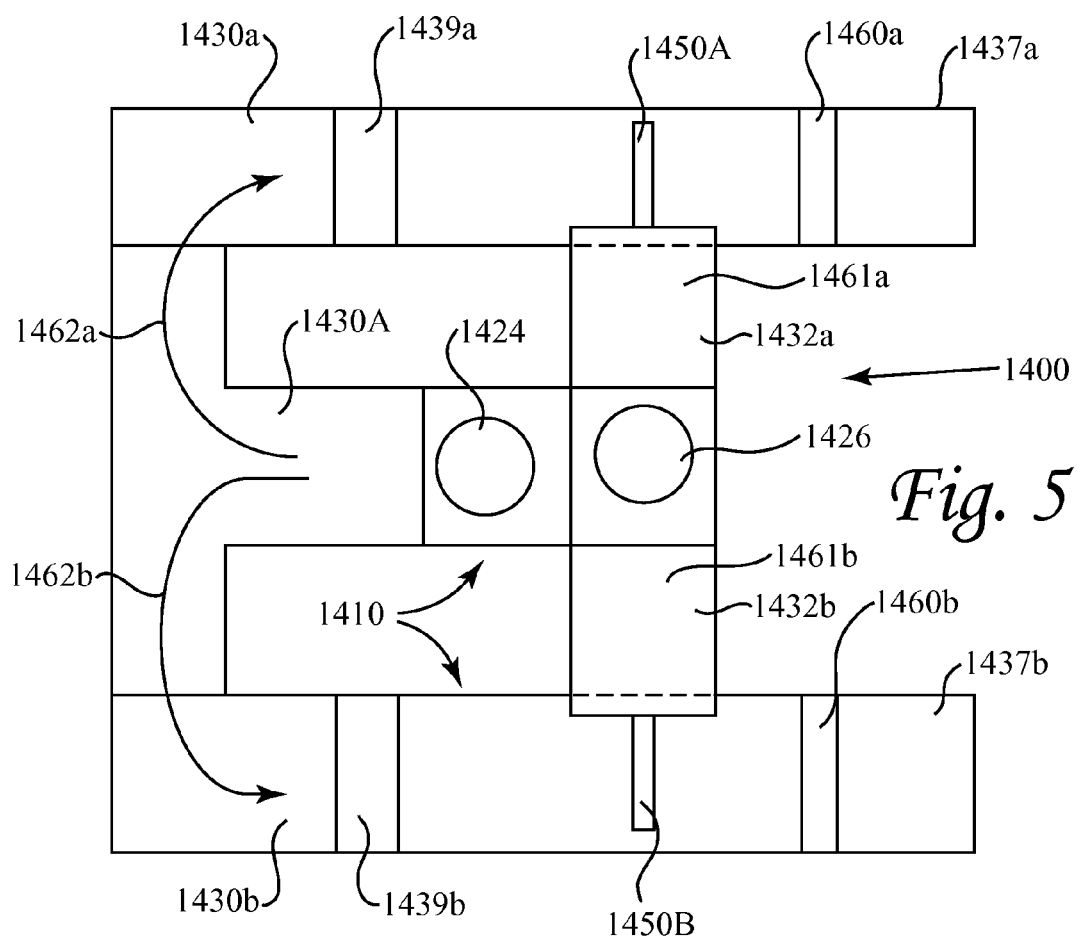
FIG. 5 is a schematic view of a fifth embodiment of the invention.

A fifth embodiment of a dry conjugate dual path immunoassay device system 1400 is seen in FIG. 5 and provides a fourth generation immunoassay device. The fifth embodiment is similar to the fourth embodiment except that two separate samples are established, two elongated paths are established for the buffer (and conjugate), and two test zones are established; typically, one for testing antigens and the other for testing antibodies. More particularly, system 1400 includes a includes a test cell 1410 with a first location 1426 for receiving a sample and a second location 1424 for receiving a buffer solution. A first sorbent or bibulous material 1432a, 1432b is provided for directing horizontal flow paths 1461a, 1461b for the sample. The first sorbent material may be made from a single piece of material or multiple pieces of material. Means discussed below with reference to FIGS. 7-9b are provided for dividing the buffer solution received at the second location 1124 such that some of the buffer solution is directed to the first sorbent material 1432a, 1432b which directs the sample, and some of the buffer solution is directed to the third sorbent or bibulous material 1430A (selected to have a slower flow characteristic than either the first sorbent material 1432a, 1432b or the second or fourth sorbent material 1430a, 1430b). In the embodiment of FIG. 5, the third sorbent material 1430A is arranged as a "T", although the material could be formed into other shapes (such as a "V", an "M", or a dash, by way of example only). Regardless, the third sorbent material 1430A is in contact with second sorbent material 1430a, 1430b (shown as two separate pieces in FIG. 5—although depending upon the arrangement of the third sorbent material, the second sorbent material could be a single piece such as in the shape of a bracket ([), an "E", by way of example only). This provides two elongated path 1462a, 1462b to the respective test zones 1433a, 1433b which are respectively located at the junction of the second sorbent material 1430a with the first sorbent material 1432a, and the junction of the second sorbent material 1430b with the first sorbent material 1432b. The test zones 1433a, 1433b include one or more test lines or indicators (e.g., 1450A, 1450B) having immobilized antigens or antibodies on either sorbent material 1430a, 1430b or sorbent material 1432a, 1432b. Preferably, control lines 1460a, 1460b is provided downstream of the test lines, and an optional reservoir or wicking zone 1437a, 1437b may be provided as well. Conjugate 1439a, 1439b having desired antigens or antibodies with attached colored markers is immobilized along the elongated paths 1462a, 1462b preferably in or on the second sorbent material 1430a, 1430b upstream of the test zones 1433a, 1433b. As shown in FIG. 5, the conjugate zones are preferably located toward the test zone ends of the elongated paths. With the provided arrangement, if sample is first deposited into the first location 1426, and buffer is then deposited in the second location 1424, the buffer will cause the sample to reach the test zones 1433a, 1433b via paths 1461a, 1461b and permit antigens and/or antibodies in the sample to bind to the antibodies and/or antigens in the test lines 1450A, 1450B in advance of the conjugate 1439a, 1439b being carried by buffer reaching the test zone via the elongated paths 1462a, 1462b.

In the fourth and fifth embodiments, the third sorbent or bibulous material which has a slower flow characteristic relative to the first sorbent material may be a small pore membrane (e.g., nitrocellulose or nylon membrane having a pore size of 3 to 30 microns), glass fibers, or cellulose, polyester, rayon or other known synthetic materials. As will be appreciated by those skilled in the art, other materials could be utilized to control the speed of the buffer flow through the third sorbent material and thereby control arrival timing of the buffer with the conjugate at the test site relative to the arrival of the sample.

A sixth embodiment of a dry conjugate dual path immunoassay device system 1500 is seen in FIG. 6 and also provides a fourth generation immunoassay device. The sixth embodiment is similar to the fifth embodiment except that instead of providing a third sorbent material having slower flow characteristics, the elongated paths for the buffer which eventually carries the conjugate are tortuous or serpentine, and are at least five times the length of the sample flow path. More particularly, system 1500 includes a includes a test cell 1510 with a first location 1526 for receiving a sample and a second location 1524 for receiving a buffer solution. A first sorbent or bibulous material with branches 1532a, 1532b is provided for directing horizontal flow paths 1561a, 1561b for the sample. The first sorbent material may be made from a single piece of material or multiple pieces of material. Means discussed below with reference to FIGS. 7-9b are provided for dividing the buffer solution received at the second location 1524 such that some of the buffer solution is directed to the first sorbent material 1532a, 1532b which directs the sample, and some of the buffer solution is directed to the second sorbent or bibulous material 1530a 1530b which provides two elongated path branches 1562a, 1562b to the respective test zones 1533a, 1533b which are respectively located at the junction a first branch of the second sorbent material 1530a with a first branch of the first sorbent material 1532a, and the junction of a second branch of the second sorbent material 1530b with a second branch of the first sorbent material 1532b. The test zones 1533a, 1533b include one or more test lines or indicators (e.g., 1550A, 1550B) having immobilized antigens or antibodies on either sorbent material 1530a, 1530b or sorbent material 1532a, 1532b. Preferably, control lines 1560a, 1560b is provided downstream of the test lines, and an optional reservoir or wicking zone 1537a, 1537b may be provided as well. Conjugate 1539a, 1539b having desired antigens or antibodies with attached colored markers is immobilized along the elongated paths 1562a, 1562b preferably in or on the second sorbent material 1530a, 1530b upstream of the test zones 1533a, 1533b. As shown in FIG. 6, the conjugate zones are preferably located toward the test zone ends of the elongated paths. With the provided arrangement, if sample is first deposited into the first location 1526, and buffer is then deposited in the second location 1524, the buffer will cause the sample to reach the test zones 1533a, 1533b via paths 1561a, 1561b and permit antigens and/or antibodies in the sample to bind to the antibodies and/or antigens in the test lines 1550A, 1550B in advance of the conjugate 1539a, 1539b being carried by buffer reaching the test zone via the elongated paths 1562a, 1562b.

In all the previous embodiments, where the test cell of the invention is provided in a housing, the housing is provided with a first opening adjacent the first location and a second opening adjacent the second location. A viewing window is provided in the housing above the test line. Where a control line is provided, the viewing window may extend over the test line and control line, or a separate viewing window may be provided over the control line.

In all of the previous embodiments, it is preferred that the locations for receiving the sample and the buffer solution are provided near or adjacent each other.

Turning now to FIGS. 7-9b, various dividers which divide the buffer solution received at the second location are provided. A first divider for the buffer solution is seen in FIG. 7 and comprises a wedge-shaped element 1601 (V-shaped or triangular in cross section) located at the location for receiving the buffer solution (e.g., at an opening in a housing), where the apex 1602 of the wedge is directed upward. As drops of buffer solution are dropped into the buffer receiving opening, the apex divides the drops into two streams. The first stream is directed to the first sorbent material. The second stream is directed to the second elongated path sorbent material. If the wedge apex is located in the middle of the buffer receiving location, half of the buffer solution is directed toward the sample receiving location and first sorbent material, and the other half is directed toward the second sorbent material. If the wedge apex is located to one side or the other, more of the buffer may be directed one way or to the other.

A second divider for the buffer solution received at the second location is shown in FIG. 8 and comprises a flow control material 1601a. Flow control material 1601a is chosen to permit buffer to flow but is resistant to receiving sample. An example would be a very small pore size material such as cotton or cellulose paper (preferably with pores less than 3 microns). The flow control material 1601a is coupled to both the sample receiving location (e.g., pad) and the second (or third) sorbent material.

A third divider 1601b for the buffer solution received at the second location is shown in FIGS. 9 and 9a and comprises an opening 1603 in a housing 1604 sized to receive the nib 1605 of a buffer dispenser, and a vertical wall 1606 recessed in the housing opening which divides the buffer solution. Preferably, the sample receiving location or pad is provided on one side of the vertical wall, and the second (or third) sorbent material is provided on the other side of the vertical wall. It will be appreciated that the wall 1606 can take any desired shape as long as it is located appropriately to divide drops of buffer being delivered by the buffer dispenser nib. Thus wall may divide the buffer solution so that approximately half of the buffer solution is directed toward the first sorbent material and the other half of the buffer solution is directed toward the second sorbent material, or may divide the buffer solution so that a desired first proportion of the buffer solution is directed toward the first sorbent material and a desired different second proportion of the buffer solution is directed toward the second sorbent material.

With respect to all of the above test cell embodiments and buffer divider embodiments, if desired, the buffer may be packaged as part of the test cell by providing a "buffer button" 1780 as seen in FIG. 10 at the second location. For example, if a housing is provided, the buffer button may constitute a module located in a housing opening above the second location. The module could constitute a flexible plastic upper member 1781 and a rupturable (e.g., foil or plastic) lower member 1782, with the buffer solution 1783 contained therebetween. As a result, when the flexible plastic upper member is pressed, the force is translated to the buffer solution which causes the lower member to rupture and release the buffer solution which is then divided by the buffer dividing means. Alternatively, contained within the module may be a dividing element (e.g., a vertical plastic element connected to the flexible plastic upper member) which causes the lower container to rupture and which will automatically divide the buffer solution contained within the module without need for a separate means for dividing the buffer solution. As another alternative, a wedge (such as wedge 1600) or a wall (such as wall 1606) contained within the housing below the buffer button can be used to rupture the lower member when the buffer button is pressed.

According to one aspect of the invention, any of the test cells described above may be used by (1) depositing a sample at the (first) location for receiving the sample, (2) depositing a predetermined amount of buffer solution at the (second) location for receiving the buffer solution, and (3) after a desired period of time, inspecting the test zone(s) and where provided the control zone(s) to determine whether the test is positive or negative. It is noted that sufficient buffer is deposited at the second location to cause the sample to move along the first sorbent material to the test zone, as well as to traverse the path of the second (and where provided, third) sorbent material and cause the conjugate to move to the test zone. Because of the arrangement of the first sorbent material as well as the second (and where provided, third) sorbent material, the sample is brought to the test zone in advance of the conjugate. The step of depositing a sample may involve depositing blood, serum, spittum, feces, or other bodily fluid at the first location via a dropper, a swab, a loop or other depositing means known in the art. The step of depositing a predetermined amount of buffer solution may comprise utilizing a dropper, pressing a buffer button, or utilizing any other depositing means known in the art.

It will be appreciated that the materials, thicknesses and lengths of the first and second sorbent materials are chosen to adjust the timing regarding the sample and conjugate reaching the test site(s).

There have been described and illustrated herein several embodiments of immunoassays and methods of their use. While particular embodiments of the invention have been described, it is not intended that the invention be limited thereto, as it is intended that the invention be as broad in scope as the art will allow and that the specification be read likewise. For example, while the specification discusses ligand binding using antigen/antibody reactions, other ligand binding mechanisms such as aptamer binding, nucleic acid binding, enzymatic binding, etc. may also be used. Also while particular buffer dividers have been described which divide the buffer for the sample flow path and the conjugate flow path, it will be appreciated that other dividers could be utilized. Further, it should be appreciated that chemical agents such as sugar, BSA, detergent, etc., or biological agents (serum, antibody, antigen) may be added in one or both of the sorbent strips in order to delay or enhance flow rate for the buffer or for the buffer/sample solution. These modifications could be additionally utilized to enhance sensitivity or block non-specific binding for the assay. It will therefore be appreciated by those skilled in the art that yet other modifications could be made to the provided invention without deviating from its spirit and scope as claimed.

What is claimed is:

1. A test device for determining the presence of a ligand in a sample, comprising:
   a) buffer solution;
   b) a first sorbent strip having a first location for receiving a sample and defining a first migration path;
   c) a second sorbent strip distinct from said first sorbent strip, said second sorbent strip having a second location for receiving said buffer solution and at least partially defining a second migration path distinct from said first migration path and elongated relative to said first migration path;
   d) a conjugate supported by said second sorbent strip;
   e) a test site located on or in at least one of said first sorbent strip and said second sorbent strip, said test site having an immobilized ligand-binding mechanism, and said first and second sorbent strips touching each other at the test site;
   f) a frangible container and divider located at said second location, said frangible container containing said buffer solution, said divider directing a first amount of said buffer solution to said first sorbent strip to move said sample to said test site and a second amount to said second sorbent strip to move said conjugate to said test site upon breaking of said frangible container; and
   g) a housing defining a first opening adjacent said first location, a second opening adjacent said second location, and a window adjacent said test site through which said test site is viewable,
      wherein said first migration path is provided with a first length and said second migration path is provided with a second length, and said first length said second length are chosen to permit said sample to reach said test site so that ligand in said sample reaches said test site and binds to said immobilized ligand-binding mechanism prior to said conjugate reaching said test site.

2. A test device according to claim 1, wherein:
said second migration path is tortuous.

3. A test device according to claim 2, wherein:
said second migration path is at least four times as long as said first migration path.

4. A test device according to claim 1, wherein:
said second sorbent strip includes a delay element.

5. A test device according to claim 1, further comprising:
a third sorbent strip distinct from said first sorbent strip and said second sorbent strip, said third sorbent strip coupling said second location to said second sorbent strip, said third sorbent strip having slower flow characteristics than said first sorbent material.

6. A test device according to claim 1, wherein:
said conjugate comprises an antigen or antibody for the ligand and a marker coupled to the antigen or antibody.

7. A test device according to claim 6, wherein:
said marker is a colored marker viewable in the visible spectrum.

8. A test device according to claim 1, wherein:
said at least one of said first and second sorbent strips includes a control site, and said housing defines a window for viewing said control site.

9. A test device according to claim 1, wherein:
said first sorbent strip has a first pore size and said second sorbent strip has a second pore size, and said first pore size is larger than said second pore size.

10. A test device according to claim 9, wherein:
said first pore size is between 3 and 20 microns, and said second pore size is between 20 and 40 microns.

11. A test device according to claim 1, wherein:
said divider comprises a wedge or a wall.

12. A test device according to claim 1, wherein:
said second location is adjacent said first location.

13. A method for testing a sample for the presence of a ligand, comprising:
   a) obtaining a test device according to claim 1;
   b) applying the sample to said first location;
   c) after said applying the sample, applying the buffer solution to the second location by breaking the frangible container; and
   d) inspecting said test site to determine an indication the presence or lack thereof of the ligand in the sample.

14. A test device for determining the presence of a ligand in a sample, said test device for use with a buffer solution and comprising:
   a) a first sorbent or bibulous material having a first location for receiving a sample and defining a first horizontal migration path for the sample;
   b) a second sorbent or bibulous material in fluid contact with said first location and defining a second horizontal migration path for the sample;
   c) a third sorbent or bibulous material distinct from said first and second sorbent or bibulous materials, said third sorbent or bibulous material receiving the buffer solution and at least partially defining a third horizontal migration path distinct from said first and second migration paths and elongated relative to said first and second migration paths;
   d) a first conjugate supported by said third sorbent or bibulous material;
   e) a fourth sorbent or bibulous material distinct from said first and second sorbent or bibulous materials, said fourth sorbent or bibulous material receiving the buffer solution and at least partially defining a fourth horizontal migration path distinct from said first and second migration paths and elongated relative to said first and second migration paths;

f) a second conjugate supported by said fourth sorbent or bibulous material;

g) a first test site located on or in at least one of said first sorbent or bibulous material and said third sorbent or bibulous material, said first test site having a first immobilized ligand-binding mechanism for detecting antibodies in the sample, and said first and third sorbent or bibulous materials touching each other at said first test site;

h) a second test site located on or in at least one of said second sorbent or bibulous material and said fourth sorbent or bibulous material, said second test site having a second immobilized ligand-binding mechanism for detecting antigens in the sample, said second and fourth sorbent or bibulous materials touching each other at said second test site; and i) a divider which directs a first amount of said buffer solution to said first and second sorbent or bibulous materials to move said sample to said first and second test sites and a second amount of said buffer solution to said third and fourth sorbent or bibulous materials to move said first and second conjugates to said first and second test sites, wherein said first migration path is provided with a first length, said second migration path is provided with a second length, said third migration path is provided with a third length, and said fourth migration path is provided with a fourth length, and said first length and said third length are chosen to permit said sample to reach said first test site so that ligand in said sample reaches said first test site and binds to said first immobilized ligand-binding mechanism prior to said first conjugate reaching said first test site, and said second length and said fourth length are chosen to permit said sample to reach said second test site so that ligand in said sample reaches said second test site and binds to said second immobilized ligand-binding mechanism prior to said second conjugate reaching said second test site.

15. A test device according to claim 14, further comprising:
a fifth sorbent or bibulous material distinct from said first, second, third and fourth sorbent or bibulous materials, said third fifth sorbent or bibulous material coupling said second location to said third sorbent or bibulous material, said fifth sorbent or bibulous material having slower flow characteristics than said first sorbent or bibulous material.

16. A test device according to claim 15, further comprising:
a sixth sorbent or bibulous material distinct from said first, second, third and fourth sorbent or bibulous strips, said sixth sorbent or bibulous material coupling said second location to said third sorbent or bibulous strip, said fifth sorbent or bibulous material having slower flow characteristics than said second sorbent or bibulous material.

17. A test device according to claim 16, wherein:
said fifth and sixth sorbent or bibulous materials have portions which are not distinct from each other.

18. A method according for testing a sample for the presence ligands, comprising:
a) obtaining a test device according to claim 14;
b) applying the sample to said first location;
c) after said applying the sample, applying the buffer solution to the second location; and
d) inspecting said first and second test sites to determine an indication the presence or lack thereof of the ligands in the sample.

19. A method according to claim 18, wherein:
said test device has a housing defining a first opening adjacent said first location, a second opening adjacent said second location, a first window adjacent said first test site through which said first test site is viewable, and a second window adjacent said second test site through which said second test site is viewable;
said applying the sample comprises depositing the sample through said first opening to said first location,
said applying the solution comprises depositing the buffer solution through said second opening to said second location, and
said inspecting comprises inspecting through said first window and through said second window.

* * * * *